US009586960B2

(12) United States Patent
Tomesch et al.

(10) Patent No.: US 9,586,960 B2
(45) Date of Patent: Mar. 7, 2017

(54) 4-((6BR,10AS)-3-METHYL-2,3,6B,9,10,10A-HEXAHYDRO-1H-PYRIDO[3',4':4,5]PYRROLO[1,2,3-DE]QUINOXALIN-8(7H)-YL)-1-(4-FLUOROPHENYL)-1-BUTANONE TOLUENESULFONIC ACID SALT CRYSTAL FORMS

(71) Applicants: John Tomesch, Succasunna, NJ (US); Lawrence P. Wennogle, Hillsborough, NJ (US)

(72) Inventors: John Tomesch, Succasunna, NJ (US); Lawrence P. Wennogle, Hillsborough, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 14/954,845

(22) Filed: Nov. 30, 2015

(65) Prior Publication Data
US 2016/0194325 A1 Jul. 7, 2016

Related U.S. Application Data

(60) Continuation of application No. 14/177,689, filed on Feb. 11, 2014, now Pat. No. 9,199,995, which is a division of application No. 12/922,056, filed as application No. PCT/US2009/001608 on Mar. 12, 2009, now Pat. No. 8,648,077.

(60) Provisional application No. 61/036,069, filed on Mar. 12, 2008.

(51) Int. Cl.
*A61K 31/4985* (2006.01)
*C07D 471/22* (2006.01)
*C07D 471/16* (2006.01)
*C07C 309/30* (2006.01)

(52) U.S. Cl.
CPC .......... *C07D 471/16* (2013.01); *C07C 309/30* (2013.01)

(58) Field of Classification Search
CPC .................... A61K 31/4985; C07D 471/22
USPC ........................................... 514/250; 544/343
See application file for complete search history.

(56) References Cited

U.S. PATENT DOCUMENTS

| 6,548,493 | B1 | 4/2003 | Robichaud et al. |
| 6,552,017 | B1 | 4/2003 | Robichaud et al. |
| 6,713,471 | B1 | 3/2004 | Robichaud et al. |
| 7,071,186 | B2 | 7/2006 | Robichaud et al. |
| 7,081,455 | B2 | 7/2006 | Robichaud et al. |
| 7,183,282 | B2 | 2/2007 | Robichaud et al. |
| RE39,679 | E | 6/2007 | Robichaud et al. |
| RE39,680 | E | 6/2007 | Robichaud et al. |
| 7,462,641 | B2 | 12/2008 | Igo et al. |
| 8,309,722 | B2 | 11/2012 | Tomesch et al. |
| 8,598,119 | B2 | 12/2013 | Mates et al. |
| 8,648,077 | B2 | 2/2014 | Tomesch et al. |
| 8,779,139 | B2 | 7/2014 | Tomesch et al. |
| 8,993,572 | B2 | 3/2015 | Mates et al. |
| 9,168,258 | B2 | 10/2015 | Mates et al. |
| 9,199,995 | B2 | 12/2015 | Tomesch et al. |
| 2014/0364609 | A1 | 12/2014 | Tomesch et al. |
| 2015/0072964 | A1 | 3/2015 | Mates et al. |
| 2015/0079172 | A1 | 3/2015 | Mates et al. |
| 2015/0080404 | A1 | 3/2015 | Mates et al. |
| 2015/0166540 | A1 | 6/2015 | Mates et al. |
| 2016/0031885 | A1 | 2/2016 | Li et al. |
| 2016/0194326 | A1 | 7/2016 | Tomesch et al. |

FOREIGN PATENT DOCUMENTS

| WO | WO 00/77001 | 12/2000 |
| WO | WO 00/77002 | 12/2000 |
| WO | WO 00/77010 | 12/2000 |

OTHER PUBLICATIONS

Balbach, et al. "Pharmaceutical evaluation of early development candidates 'the 100 mg-approach' ", International Journal of Pharmaceutics, vol. 275, pp. 1-12 (2004).
Bastin, "Salt Selection and Optimized Procedures for Pharmaceutical New Chemical Entities", Organic Process and Research Development, vol. 4, No. 5, pp. 427-435 (2000).
Byrn, "Pharmaceutical Solids: A Strategic Approach to Regulatory Considerations", vol. 12, No. 7, p. 945-954 (1995).
Grant, "Polymorphism in Pharmaceutical Solids", Chapter 1, pp. 1-10 (1999).
Guillory, "Polymorphism in Pharmaceutical Solids", Chapter 5, pp. 183-226 (1999).
Hackman, et al. JAMA, 296(14), 2006, 1731-1732.
Haynes, "Occurrence of Pharmaceutically Acceptable Anions and Cations in the Cambridge Database", Journal of Pharmaceutical Sciences, vol. 94, No. 10, pp. 2111-2120 (2005).
Jain et al., "Polymorphism in Pharmacy", Indian Drugs, 23(6), 315-316 (1986).
Jordan, V.C. Nature Reviews: Drug Discovery, 2, 2003, 205.
Li et al., "Discovery of a Tetracyclic Quinoxaline Derivative as a Potent and Orally Active Multifunctional Drug Candidate for the Treatment of Neuropsychiatric and Neurological Disorders", vol. 57, pp. 2670-2682 (2014).
Newman et al., "Solid-state analysis of the active pharmaceutical ingredient in drug products", Drug Discovery Today, vol. 8, No. 9, 898-903 (2003).
Savjani et al., "Drug Solubility: Importance and Enhancement Techniques", International Scholarly Research Network Pharmaceutics (2012), vol. 2012, pp. 1-10.
Singhal et al., "Drug polymorphism and dosage form design: a practical perspective", Advanced Drug Delivery Reviews, vol. 56, pp. 335-347 (2004).
Skoog, "Principles of Instrumental Analysis, $4^{th}$ Edition", p. 577 (1992).
Smith, A.D., et al., "Oxford Dictionary of Biochemistry and Molecular Biology", Oxford University Press, p. 145, (1997).
Snyder et al., "Functional profile of a novel modulator of serotonin, dopamine, and glutamate neurotransmission", Psychopharmacology, 232:605-621 (2015).
Snyder et al., "Functional profile of a novel modulator of serotonin, dopamine, and glutamate neurotransmission", Psychopharmacology, Published online Aug. 2014, DOI 10.1007/s00213-014-3704-1.

Primary Examiner — Douglas M Willis
(74) Attorney, Agent, or Firm — Hoxie & Associates LLC

(57) ABSTRACT

The present invention relates to toluenesulfonic acid addition salt crystals of 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone, and methods of using such crystals as 5-hydroxytryptamine 2 receptor agonists and antagonists in treating disorders of the central nervous system.

2 Claims, 12 Drawing Sheets

4-((6BR,10AS)-3-METHYL-2,3,6B,9,10,10A-HEXAHYDRO-1H-PYRIDO[3',4':4,5] PYRROLO[1,2,3-DE] QUINOXALIN-8(7H)-YL)-1-(4-FLUOROPHENYL)-1-BUTANONE TOLUENESULFONIC ACID SALT CRYSTAL FORMS

CROSS-REFERENCE TO RELATED APPLICATIONS

This application is a continuation of Ser. No. 14/177,689, filed on Feb. 11, 2014, which is a divisional of Ser. No. 12/922,056, now granted as U.S. Pat. No. 8,648,077, which was filed Sep. 10, 2010 under 35 U.S.C §371 which claims benefit to PCT Application No. PCT/US2009/001608, filed on Mar. 12, 2009 which claims the benefit of U.S. Provisional Patent Application No. 61/036,069, filed Mar. 12, 2008, the contents of each of which are hereby incorporated by reference in their entireties.

FIELD OF THE INVENTION

The present invention relates to toluenesulfonic acid addition salt crystals of specific substituted heterocycle fused gamma-carbolines, the method of making and using such crystals.

BACKGROUND OF THE INVENTION

Substituted heterocycle fused gamma-carbolines and their pharmaceutically acceptable salts are represented by the core structure shown in Formula 1 J:

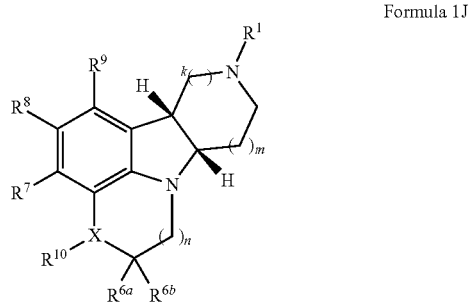

Formula 1J

These compounds are disclosed in WO 2000/77010; WO 2000/77002; WO 2000/77001; U.S. Pat. Nos. 6,713,471; 6,552,017; 7,081,455; 6,548,493, 7,071,186; Reissue U.S. Pat. Nos. 39,680; 39,679; and U.S. Provisional Application No. 60/906,473, the contents of each of which are herein incorporated by reference in their entirety. These compounds have been found to be useful as 5-$HT_2$ receptor agonists and antagonists used in treating disorders of the central nervous system including a disorder associated with 5HT2C or 5HT2A receptor modulation selected from obesity, anorexia, bulimia, depression, a anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, gastrointestinal disorders such as dysfunction of the gastrointestinal tract motility.

As a free base, substituted heterocycle fused gamma-carbolines exist in liquid form and are susceptible to N-oxidation and/or degradation. Such unstable characteristics could render these compounds undesirable as pharmaceutical products. The prior art discloses a large number of substituted heterocycle fused gamma-carboline derivatives in free base form as well as a large number of pharmaceutically acceptable salts, including hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Of the large numbers of possible pharmaceutically acceptable salt compounds disclosed in the prior art, none were shown to have particular stability or desired properties. Because many pharmaceutical compounds can exist in different physical forms (e.g., liquid or solid in different crystalline, amorphous, polymorphous, hydrate or solvate forms) which can vary the stability, solubility, bioavailability or pharmacokinetics (absorption, distribution, metabolism, excretion or the like) and/or bioequivalency of a drug, it is of critical importance in pharmaceutical development to identify a pharmaceutical compound of optimal physical form (e.g., free base or salt in solid, liquid, crystalline, hydrate, solvate, amorphous or polymorphous forms).

SUMMARY OF THE INVENTION

We have surprisingly found that a particular substituted heterocycle fused gamma-carboline is especially stable in toluenesulfonic acid addition salt form and is especially advantageous in the preparation of galenic formulations of various and diverse kind. The present invention therefore provides 4-((6bR,10aS)-3-methyl-2,3,6b,9,10,10a-hexahydro-1H-pyrido[3',4': 4,5]pyrrolo[1,2,3-de]quinoxalin-8 (7H)-yl)-1-(4-fluorophenyl)-1-butanone tosylate salt in solid form ("Solid Salt of the Present Invention"). In particular, the present invention provides 4-((6bR,10aS)-3-methyl-2,3, 6b,9,10,10a-hexahydro-1H-pyrido[3',4': 4,5]pyrrolo[1,2,3-de]quinoxalin-8(7H)-yl)-1-(4-fluorophenyl)-1-butanone tosylate salt crystal ("Salt Crystals of the Present Invention"). It has been surprisingly found that the Salts Crystals of the Present Invention are especially stable and preferred for galenic and/or therapeutic use. The invention therefore provides the following:

1.1 Salt Crystals of the Present Invention in dry crystalline form;
1.2 Salt Crystals of the Present Invention or formula 1.1, in needle form;
1.3 Salt Crystals of the Present Invention or formula 1.1, in flake form (e.g., thin flakes or flake fragments);
1.4 Salt Crystals of the Invention or any of formulae 1.1-1.2, wherein said Salt Crystals are in a single crystal form and are free or substantially free of any other form, e.g., free or substantially free, e.g., less than 10 wt. %, preferably less than about 5 wt. %, more preferably less than about 2 wt. %, still preferably less than about 1 wt. %, still preferably less than about 0.1%, most preferably less than about 0.01 wt. % of amorphous form;
1.5 Salt Crystals of the Invention or any of formulae 1.1-1.4, wherein said Salt Crystals are in a single crystal form and are free or substantially free of any other form, e.g., less than 10 wt. %, preferably less than about 5 wt. %, more preferably less than about 2 wt. %, still preferably less than about 1 wt. %, still preferably less than about 0.1%, most preferably less than about 0.01 wt. % of other crystal forms;

1.6 Salt Crystals of the Invention or any of formulae 1.1-1.4, wherein said Salt Crystals are in a single crystal form and are free or substantially free of any other form, e.g., less than 10 wt. %, preferably less than about 5 wt. %, more preferably less than about 2 wt. %, still preferably less than about 1 wt. %, still preferably less than about 0.1%, most preferably less than about 0.01 wt. % of amorphous and other crystal forms;

1.7 Salt Crystals of the Invention or any of formulae 1.1-1.6, wherein said Salt Crystals are in a non-solvate or non-hydrate form;

1.8 Salt Crystals of the Invention or any of formulae 1.1-1.7, wherein said Salt Crystals are in a non-solvate and non-hydrate form;

1.9 Salt Crystals of the Present Invention or any of formulae 1.1-1.8, wherein said Salt Crystals exhibit an X-ray powder diffraction pattern comprising at least two 2-theta values selected from those set forth below ("Crystal Form A"):

| Position (°2θ) | D-spacing (Å) | Relative Intensity (%) |
|---|---|---|
| 5.68 | 15.543 | 100.0 |
| 12.11 | 7.303 | 26.0 |
| 16.04 | 5.520 | 22.3 |
| 17.03 | 5.202 | 66.8 |
| 18.16 | 4.882 | 21.6 |
| 19.00 | 4.668 | 20.8 |
| 21.67 | 4.097 | 15.7 |
| 22.55 | 3.940 | 23.9 |
| 23.48 | 3.786 | 18.9 |
| 24.30 | 3.660 | 23.5 |

1.10 Salt Crystals of the Present Invention or any of formulae 1.1-1.9, wherein said Salt Crystals exhibit an X-ray powder diffraction pattern comprising at least five 2-theta values selected from those set forth below ("Crystal Form A"):

| Position (°2θ) | D-spacing (Å) | Relative Intensity (%) |
|---|---|---|
| 5.68 | 15.543 | 100.0 |
| 12.11 | 7.303 | 26.0 |
| 16.04 | 5.520 | 22.3 |
| 17.03 | 5.202 | 66.8 |
| 18.16 | 4.882 | 21.6 |
| 19.00 | 4.668 | 20.8 |
| 21.67 | 4.097 | 15.7 |
| 22.55 | 3.940 | 23.9 |
| 23.48 | 3.786 | 18.9 |
| 24.30 | 3.660 | 23.5 |

1.11 Salt Crystals of the Present Invention or any of formulae 1.1-1.10, wherein said Salt Crystals exhibit an X-ray powder diffraction pattern substantially as herein set forth below ("Crystal Form A"):

| Position (°2θ) | D-spacing (Å) | Relative Intensity (%) |
|---|---|---|
| 5.68 | 15.543 | 100.0 |
| 12.11 | 7.303 | 26.0 |
| 16.04 | 5.520 | 22.3 |
| 17.03 | 5.202 | 66.8 |
| 18.16 | 4.882 | 21.6 |
| 19.00 | 4.668 | 20.8 |
| 21.67 | 4.097 | 15.7 |
| 22.55 | 3.940 | 23.9 |
| 23.48 | 3.786 | 18.9 |
| 24.30 | 3.660 | 23.5 |

1.12 Salt Crystals of the Invention or any of formulae 1.1-1.11, wherein said Salt Crystals exhibit an X-ray powder diffraction pattern substantially as herein set forth in Table 4 and/or FIG. 7 ("Crystal Form A");

1.13 Salt Crystals of the Invention or any of formulae 1.1-1.11, wherein said Salt Crystals exhibit an X-ray powder diffraction pattern substantially as herein set forth in FIG. 7A ("Crystal Form A");

1.14 Salt Crystals of the Present Invention or any of formulae 1.1-1.8, wherein said Salt Crystals exhibit an X-ray powder diffraction pattern comprising at least two 2-theta values selected from those set forth 7B;

1.15 Salt Crystals of the Present Invention or any of formulae 1.1-1.8, wherein said Salt Crystals exhibit an X-ray powder diffraction pattern substantially as herein set forth in FIG. 7B ("Crystal Form A");

1.16 Salt Crystals of the Invention or any of formulae 1.1-1.15, wherein said Salt Crystals exhibit a differential scanning calorimetry (DSC) pattern comprising a single endotherm with an onset temperature range of about 178° C.-179° C. (e.g., 178.8° C.) ("Crystal Form A");

1.17 Salt Crystals of the Invention or any of formulae 1.1-1.16, wherein said Salt Crystals exhibit a differential scanning calorimetry (DSC) pattern comprising a single endotherm with a peak temperature range of about 180° C.-181° C. (e.g., 180.8° C.) ("Crystal Form A");

1.18 Salt Crystals of the Invention or any of formulae 1.1-1.17, wherein said Salt Crystals exhibit a differential scanning calorimetry (DSC) pattern comprising a single endotherm with an enthalpy of transition (ΔH) of about 60-65 J/g, preferably about 62-64 J/g, most preferably about 63-64 J/g, e.g., about 63 J/g (e.g., 63.6 J/g) ("Crystal Form A");

1.19 Salt Crystals of the Invention or any of formulae 1.1-1.18, wherein said Salt Crystals exhibit a differential scanning calorimetry (DSC) pattern substantially as herein setforth in FIG. 8 ("Crystal Form A");

1.20 Salt Crystals of the Invention or any of formulae 1.1-1.19, wherein said Salt Crystals exhibit a differential scanning calorimetry (DSC) pattern as herein setforth in FIG. 8 ("Crystal Form A");

1.21 Salt Crystals of the Invention or any of formulae 1.1-1.20, wherein said Salt Crystals exhibits a thermogravimetric analysis profile comprising two regions of weight loss with a total weight loss of about 0.5% (e.g., 0.46%) through 200° C. ("Crystal Form A");

1.22 Salt Crystals of the Invention or any of formulae 1.1-1.21, wherein said Salt Crystals exhibits a thermogravimetric analysis profile substantially as herein setforth in FIG. 8 ("Crystal Form A");

1.23 Salt Crystals of the Invention or any of formulae 1.1-1.22, wherein said Salt Crystals exhibits a thermogravimetric analysis profile as herein setforth in FIG. 8 ("Crystal Form A");

1.24 Salt Crystals of the Invention or any of formulae 1.1-1.23, wherein said Salt Crystals have an infrared spectrum comprising at least two bands, e.g., at least five bands selected from the bands as set forth in Table 1 ("Crystal form A");

1.25 Salt Crystals of the Invention or any of formulae 1.1-1.24, wherein said Salt Crystals exhibit a Fourier Transform Infrared Spectrometry Band pattern substantially as herein set forth in Table 1 ("Crystal Form A");

1.26 Salt Crystals of the Invention or any of formulae 1.1-1.25, wherein said Salt Crystals have a melting point in the range of about 176° C. to about 181° C.

1.27 Salt Crystals of the Invention or any of formulae 1.1-1.26 wherein said Salt Crystals exhibit any combination of characterisitics as described in 1.1-1.26 ("Crystal Form A");

1.28 Crystals of the Invention or any of formulae 1.1-1.8, wherein said Salt Crystal exhibit an X-ray powder diffraction pattern substantially as herein set forth in Table 5 or FIG. 9 or 10 ("Crystal Form B");

1.29 Crystals of the Invention when made by any of processes 2.1-2.9.

The invention also provides the following:

2.1 A process for the production of Salt Crystals of the Present Invention, e.g., any of formulae 1.1-1.28, which process comprises the steps of:
  a) reacting 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone free base ("Free Base of the Present Invention") with p-toluenesulfonic acid; or
  b) dissolving 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone toluenesulfonic acid addition salt ("Salt of the Present Invention") in a solvent; and
  c) optionally cooling said reaction mixtures, e.g., to 0°-25° C.;

2.2 Process 2.1, wherein said solvent is selected from $C_{1-4}$alcohol (e.g., methanol, ethanol, isopropyl alcohol), acetone, ethyl acetate, n-propyl acetate, acetonitrile, tetrahydrofuran, butanone, heptane, hexane, water, toluene and mixtures thereof;

2.3 Process 2.1 or 2.2, wherein said solvent is selected from $C_{1-4}$alcohol (e.g., methanol, ethanol, isopropyl alcohol), acetone, ethyl acetate, n-propyl acetate, acetonitrile, tetrahydrofuran and mixtures thereof;

2.4 Process 2.1, 2.2 or 2.3, wherein said solvent is ethanol;

2.5 Process 2.1, 2.2 or 2.3, wherein said solvent is 2-propanol;

2.6 Any of Processes 2.1-2.5, which process further comprises the step of adding an anti-solvent;

2.7 Process 2.6, wherein said anti-solvent is selected from butanone, hexane, heptane, toluene and water;

2.8 A process for the production of Salt Crystal Form A, e.g., any of formulae 1.1-1.27, comprising the step of
  (a) reacting 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone free base with p-toluenesulfonic acid, e.g., p-toluenesulfonic acid monohydrate, in isopropyl alcohol, preferably in 2-5 mL, preferably 3.5 mL of isopropanol per gram of said free base to form the salt crystals;
  (b) optionally cooling said reaction mixture, e.g., cooling to 0°-25° C.

2.9 A process for the production of Salt Crystal Form B comprising the step of
  (a) reacting 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone with p-toluenesulfonic acid e.g., p-toluenesulfonic acid monohydrate in ethyl alcohol, preferably in 2-5 mL, preferably 3 mL of ethanol per gram of said free base to form the salt crystals; and
  (b) optionally cooling said reaction mixture, e.g., cooling to 0°-25° C.

2.10 A pharmaceutical composition comprising Salt Crystals of the Present Invention, e.g., any of formulae 1.1-1.29, as active ingredient, together with a pharmaceutically acceptable diluent or carrier;

2.11 A pharmaceutical composition comprising Salt Crystals of the Present Invention, e.g., any of formulae 1.1-1.29, as active ingredient, together with a pharmaceutically acceptable diluent or carrier wherein said composition is predominantly, or is entirely or substantially entirely, in dry crystalline form;

2.12 A Crystalline Solid of the Present Invention, e.g., any of formulae 1.1-1.29, for use as a pharmaceutical, e.g., for use in method of 2.13-2.2.14, or for use in the manufacture of a medicament for treating an indication as set forth in 2.13-2.2.14;

2.13 A method for the prophylaxis or treatment of a human suffering from a disorder selected from obesity, anorexia, bulimia, depression, a anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, gastrointestinal disorders such as dysfunction of the gastrointestinal tract motility, comprising administering to a patient in need thereof a therapeutically effective amount of the Salt Crystals of the Present Invention, e.g., any of formulae 1.1-1.29 or 2.12, a pharmaceutical composition as described in formula 2.10 or 2.11 or crystals formed from the process as described in formula 2.1-2.9;

2.14 Formula 2.13, wherein said disorder is sleep disorders or psychosis.

2.15 A method for the prophylaxis or treatment a disorder selected from obesity, anorexia, bulimia, depression, a anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, gastrointestinal disorders such as dysfunction of the gastrointestinal tract motility, comprising administering to a patient in need thereof a therapeutically effective amount of the Salt Crystals of the Present Invention, e.g., any of formulae 1.1-1.29 or 2.12, a pharmaceutical composition as described in formula 2.10 or 2.11 or crystals formed from the process as described in any of formulae 2.1-2.9;

2.16 Formula 2.15, wherein said disorder is sleep disorders or psychosis.

DETAIL DESCRIPTION

Figure 1:
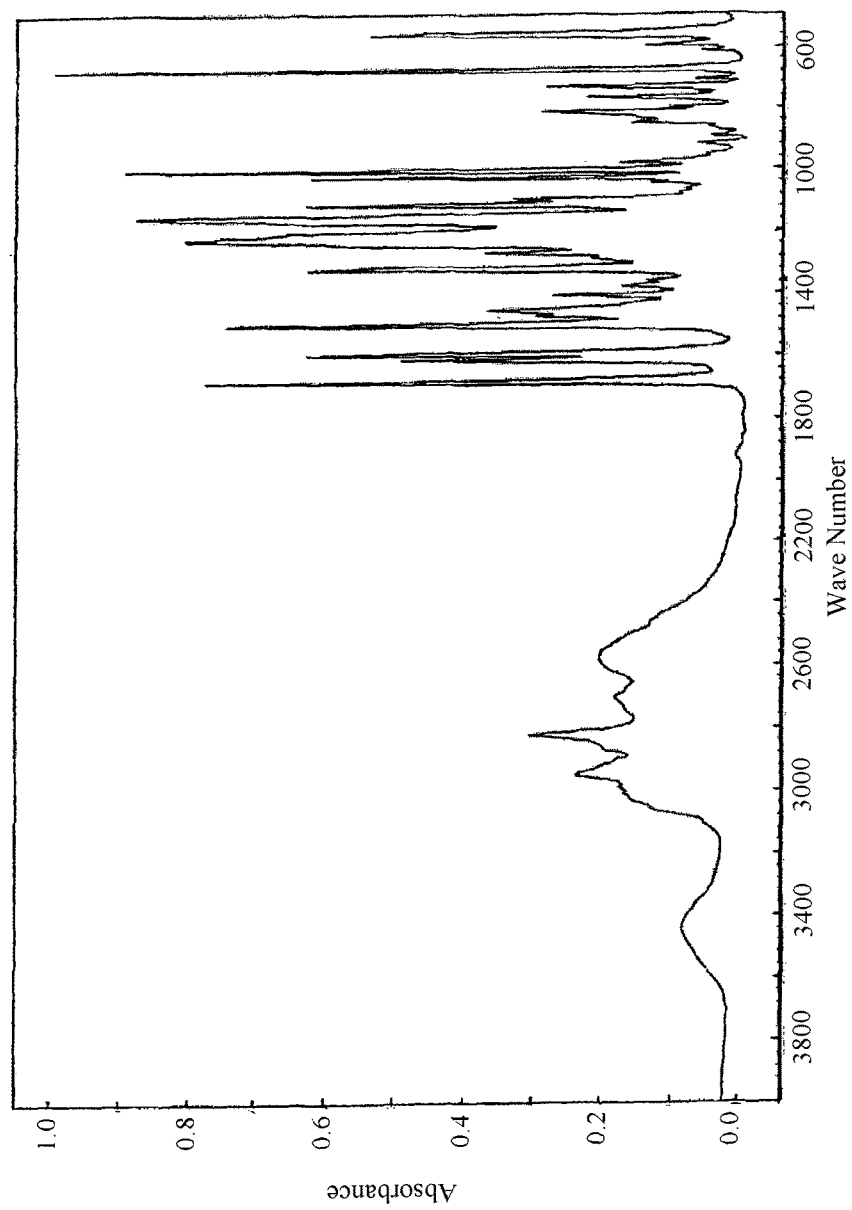
FIG. 1 (1/12) depicts an infrared spectrum of Salt Crystals Form A prepared as a KBr pellet.

As use herein, the term "crystal" or "crystals" or "crystalline" or "crystalinic" refers to any solid that has a short or long range order of the molecules, atoms or ions in a fixed lattice arrangement. Salt Crystals of the Present Invention may be in a single crystal form. Therefore, the Salt Crystals of the Present Invention may be in a triclinic, monoclinic, orthorhombic, tetragonal, rhobohedral, hexagonal or cubic crystal form or mixtures thereof. In particular, the Salt Crystals of the Present Invention are dry crystalline form. In another embodiment, the Salt Crystals of the Present Invention are in needle form. In still another embodiment, the Salt Crystals of the Present Invention are in thin flak or flake fragment form. In a particular embodiment, the Salt Crystals of the Present Invention are substantially free of other forms, e.g., free of amorphous or other crystal forms.

The term "substantially free" of other crystal forms refer to less than about 10 wt. %, preferably less than about 5 wt. %, more preferably less than about 2 wt. %, still preferably less than about 1 wt. %, still preferably less than about 0.1%, most preferably less than about 0.01 wt. % of other crystal forms, e.g., amorphous or other crystal forms. For example, the Salt Crystals of the Present Invention is in Form A and are free or substantially free of other salt forms, e.g., greater than 90 wt. % of Form A with less than 10 wt. % of the amorphous or other crystal forms. In another example, the Salt Crystals of the Present Invention is in Form B free or substantially free of other salt forms, e.g., greater than 90 wt. % of Form B with less than 10 wt. % of the amorphous or other crystal forms. Preferably, the Salt Crystals of the Present Invention comprises greater than 99 wt. % a single crystal form. Similar to "substantially free"

The term "predominantly" or "substantially entirely in a single form" refers to less than about 10 wt. %, preferably less than about 5 wt. %, more preferably less than about 2 wt. %, still preferably less than about 1 wt. %, still preferably less than about 0.1%, most preferably less than about 0.01 wt. % of other crystal forms, e.g., amorphous or other crystal forms. For example, the Salt Crystals of the Present Invention is in Form A and are free or substantially free of other salt forms, e.g., greater than 90 wt. % of Form A with less than 10 wt. % of the amorphous or other crystal forms. In another example, the Salt Crystals of the Present Invention is in Form B free or substantially free of other salt forms, e.g., greater than 90 wt. % of Form B with less than 10 wt. % of the amorphous or other crystal forms. Preferably, the Salt Crystals of the Present Invention comprises greater than 99 wt. % a single crystal form.

The term "patient" includes human or non-human.

The term "solvate" refers to crystalline solid adducts containing either stoichiometric or nonstoichiometric amounts of a solvent incorporated within the crystal structure. Therefore, the term "non-solvate" form herein refers to salt crystals that are free or substantially free of solvent molecules within the crystal structures of the invention. Similarly, the term "non-hydrate" form herein refers to salt crystals that are free or substantially free of water molecules within the crystal structures of the invention.

The term "amorphous" form refers to solids of disordered arrangements of molecules and do not possess a distinguishable crystal lattice.

The crystallinity or the morphology of the Salt Crystals of the Present Invention may be determined by a number of methods, including, but not limited to single crystal X-ray diffraction, X-ray powder diffraction, polarizing optical microscopy, thermal microscopy, differential scanning calorimetry (DSC), thermogravimetric analysis (TGA), infrared adsorption spectroscopy and Raman spectroscopy. Characterization of solvates or hydrates or lack thereof may also be determined by DSC and/or TGA.

The Solid Salt of the Present Invention may be obtained by methods generally known in the art and provided in U.S. Pat. No. WO 2000/77010; WO 2000/77002; WO 200077001; U.S. Pat. Nos. 6,713,471; 6,552,017; 7,081,455, 7,071,186; reissued U.S. Pat. Nos. 39,680; 39,679, e.g., reacting the free base with the toluenesulfonic acid monohydrate in a solvent, e.g., methanol, ethanol, isopropol, ethyl acetate, methylene chloride, toluene, tetrahydrofuran, acetone, acetonitrile, water or the like.

Crystallization methods are also well known in the art. Crystallization of the Salt of the Present Invention may be performed by either reacting the Free Base of the Present Invention with the toluenesulfonic acid, e.g., toluenesulfonic acid monohydrate in a solvent, e.g., $C_{1-4}$alcohol (e.g., methanol, ethanol, isopropyl alcohol), acetone, ethyl acetate, n-propyl acetate, acetonitrile and tetrahydrofuran and optionally cooling said solution down, e.g., to 0°-25° C.

Alternative to starting with the free base, crystallization of the Salts of the present invention may be carried out by first dissolving the salt, e.g., the Salts or Salt Crystals of the Current Invention, e.g., any of formulae 1.1-1.29, in a single solvent, e.g., $C_{1-4}$alcohol (e.g., methanol, ethanol, isopropyl alcohol), acetone, ethyl acetate, n-propyl acetate, acetonitrile and tetrahydrofuran, preferably, optionally at an elevated temperature, e.g., greater than 25° C., e.g., at 30°-75° C., preferably in a minimum amount of solvent (i.e., saturate the solution). Crystallization may then be induced by a number of ways, e.g., in a single solvent system by (a) allowing the solvent to evaporate slowly until crystals are formed; (b) slowing down the rate of stirring or stopping agitation completely; (c) cooling the solution down, e.g., to less than 25° C., e.g., to −10°-20° C.; (d) adding crystal seeds, e.g., preferably, but not necessarily, the crystal of the compound which is being crystallized; or any combinations thereof; or in a multi-solvent system by adding an anti-solvent(s), preferably a solvent having different polarity from the dissolution or the main solvent, e.g., water, heptane, hexane, butanone, or toluene or mixtures thereof to a solution of the compound in a methanol, ethanol or tetrahydrofuran solvent system.

In a particular embodiment, the Salt Crystals Form A of the Present Invention may be prepared by reacting 4-((6bR, 10aS)-3-methyl-2,3,6b,9,10,10a-hexahydro-1H-pyrido[3', 4': 4,5]pyrrolo[1,2,3-de]quinoxalin-8(7H)-yl)-1-(4-fluorophenyl)-1-butanone free base with a stoichiometric amount of p-toluenesulfonic acid monohydrate in about 2-5 mL/g, preferably 3.5 mL/g of isopropanol per gram of the Free Base of the Present Invention and optionally cooling said solution until crystals start to form, e.g., to 15-25° C. Optionally, the solution may be seeded with the Salt Crystals of the Present Invention (if available).

In another embodiment of the invention, Salt Crystals Form B may be prepared by reacting 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone free base in ethanol, e.g., 2-5 mL/g, preferably 3 mL/g of ethanol per gram of the free base with a stoichiometric amount of p-toluenesulfonic acid monohydrate. Optionally, another 0.5-1 mL of ethanol per gram of free base may be added and the mixture is cooled, e.g., to less than 25° C., e.g., about 10° C. until crystals are formed.

EXAMPLE 1

Preparation of the Salt Crystals Form A

Figure 2:
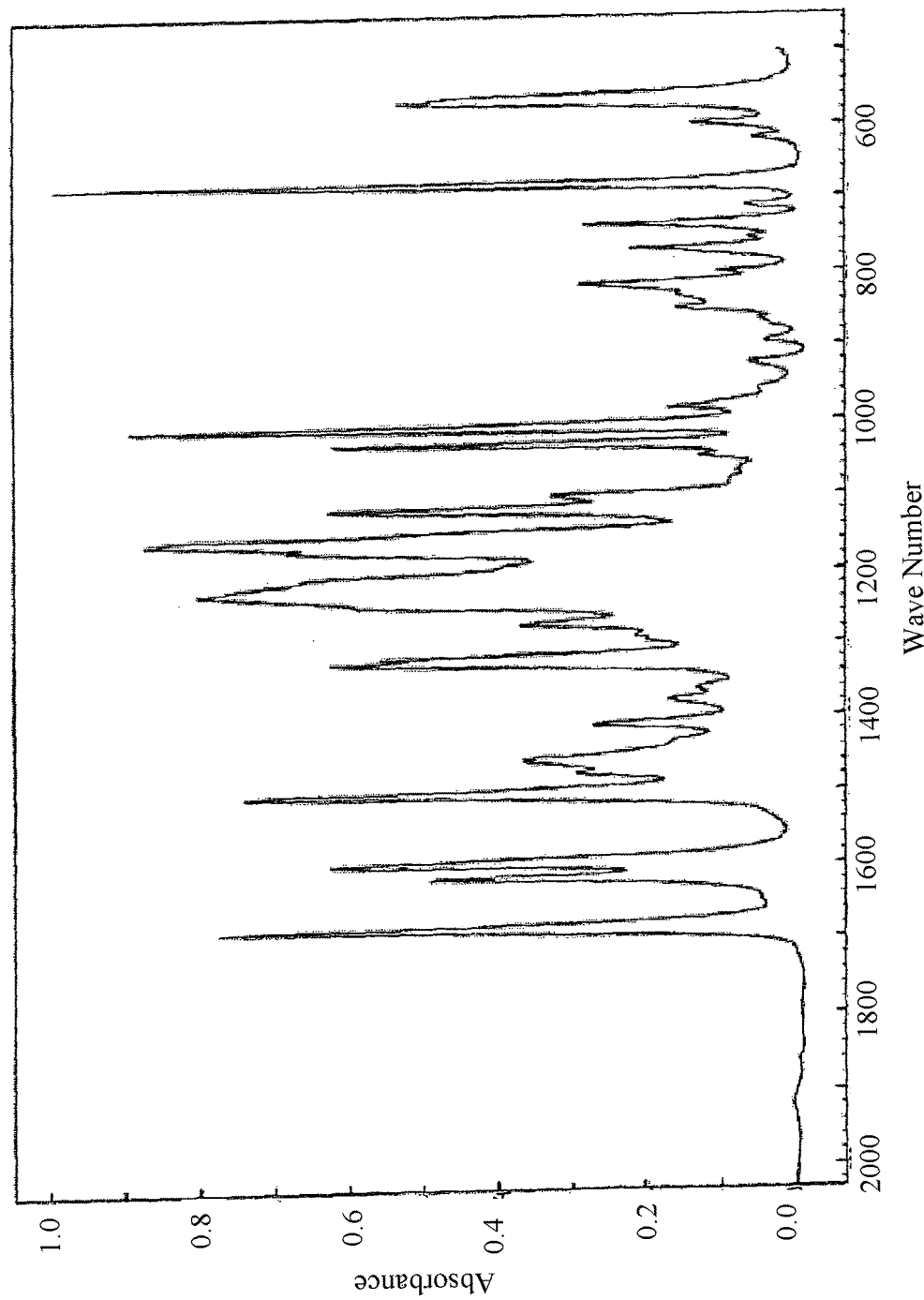
FIG. 2 (2/12) depicts an infrared spectrum finger print region of Salt Crystals Form A prepared as a KBr pellet.

Dissolve the stating material, 4-((6bR,10aS)-3-methyl-2, 3,6b,9,10,10a-hexahydro-1H-pyrido[3',4': 4,5]pyrrolo[1,2, 3-de]quinoxalin-8(7H)-yl)-1-(4-fluorophenyl)-1-butanone (free base) (178.4 g, 0.453 mol, 1 eq) in 2-Propanol (624.4 mL, 3.5 mL mLtg). Add charcoal (10 g) and stir the resulting mixture for 10-20 minutes at room temperature. After this time, remove charcoal by filtration. Wash the filter cake with 2-Propanol (89.2 mL, 0.5 mL/g SM). Transfer the combined filtrate to a 3 L 3-neck round bottom flask equipped with a mechanical stirrer, nitrogen inlet, drying tube and thermocouple and placed in a cooling tub. Add the p-Toluenesulfonic acid monollydrate (86.24 g, 0.453 mol, 1 equivalent) in one portion (reaction exotherms to 33° C., clear dark brown is observed). Cool this solution to 15-25° C. using cold tap water. Seed the resulting solution or wait until solids start to form (usually takes 30-60 minutes). Thick beige/gray paste forms. Stir the resulting paste for a minimum of 3 hours at 15-25° C. Collect the solids by filtration (filtration and followed washes are quite slow). Wash the solids with 2-Propanol (2×150 mL, room temperature), and then with heptane (room temperature, 2×150 mL). Dry the solids in a vacuum oven at 35° C. to a constant weight. Yield: 214 g, 0.378 mol, 83.4%. HPLC=93.2% purity. Chiral HPLC=de 100%. Melting Point 179°-181° C. The following characterization is performed:

Infrared Spectroscopy:

Two to six milligrams of sample are ground with ca. 200 mg of KBr. The KBr pellet spectrum is obtained on a small sample of this mixture pressed into a suitable pellet using a Wilk's mini-press. The spectrum is defined by 16 scans at 2 $cm_{-1}$ resolution. The spectrum is disclosed in FIG. 1. Infrared spectra for Salt Crystal Form A (FIG. 1 and FIG. 2) are consistent with the tosylate Salt structure. Selected infrared bands and their attributes are listed in Table 1.

TABLE 1

Tentative Fourier Transform Infrared Spectrometry Band Assignments for Salt Crystals Form A

| BAND | TENTATIVE ASSIGNMENT |
|------|----------------------|
| 2952 | C—$H_3$, wag |
| 2824 | C—H, stretch |
| 2581 | C—N, stretch |
| 1687 | C=O, stretch |
| 1617 | C=C, aromatic, bend |
| 1599 | C=C, aromatic bend |
| 1506 | C=C, aromatic, stretch |
| 1328 | S=O, bend |
| 1231 | S=O, bend |
| 1162 | C—N, stretch |
| 1010 | S=O, stretch |
| 817 | C—H, aromatic, stretch |
| 681 | C—H, bend |
| 569 | C—F, stretch |

Mass Spectrometry

Figure 3:
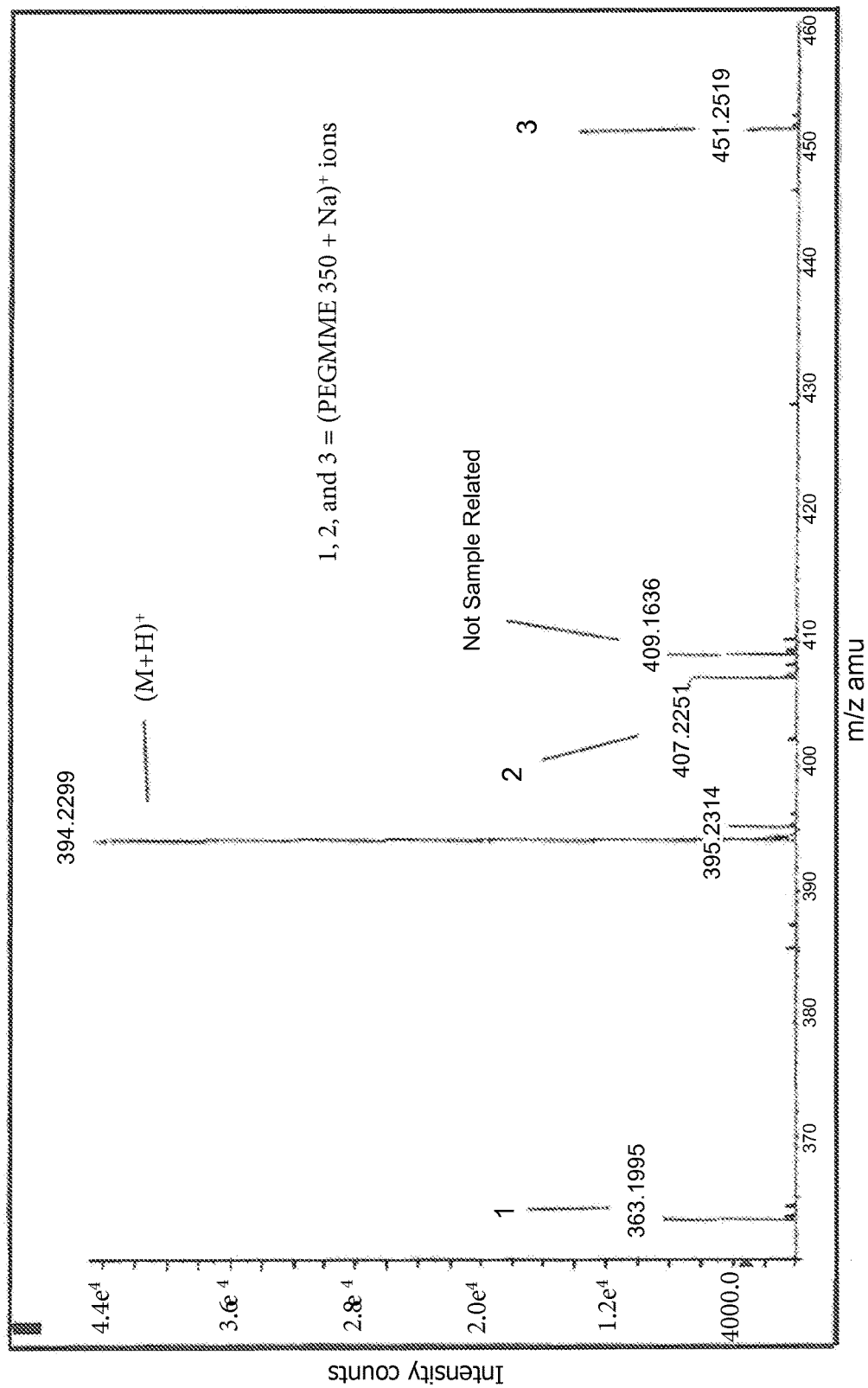
FIG. 3 (3/12) depicts a mass spectrum of Salt Crystals Form A. Peaks labeled 1, 2 and 3 are (PEGMME 350+Na)$^+$ ions.

Positive ion electrospray high-resolution mass spectrometry is carried out on Salt Crystals Form A (dissolved in 1:1 Acetonitrile: Water) with a PE Sciex Q-Star hybrid quadruple/time of flight mass spectrometer. The mass spectrometer is internally calibrated using poly (ethylene gycol) monomethyl ether 350 (PPGMME 350). Two PEGMME 350 signals at m/z 363.1995 and 451.2519 are used to measure a (PEGMME350+Na)+ signal. This gave a value of 407.2261 which compares well with the calculated value of 407.2257. The sample signal is measured in a similar way and gives a value of m/z 394.2299, which is 1.0 ppm from the calculated value of 394.2295 for the protonated molecular ion of the free base. The interpretation of mass spectra (FIG. 3) Salt Crystals Form A conforms with the expected results based on the chemical structure.

NMR Spectroscopy

Figure 4:
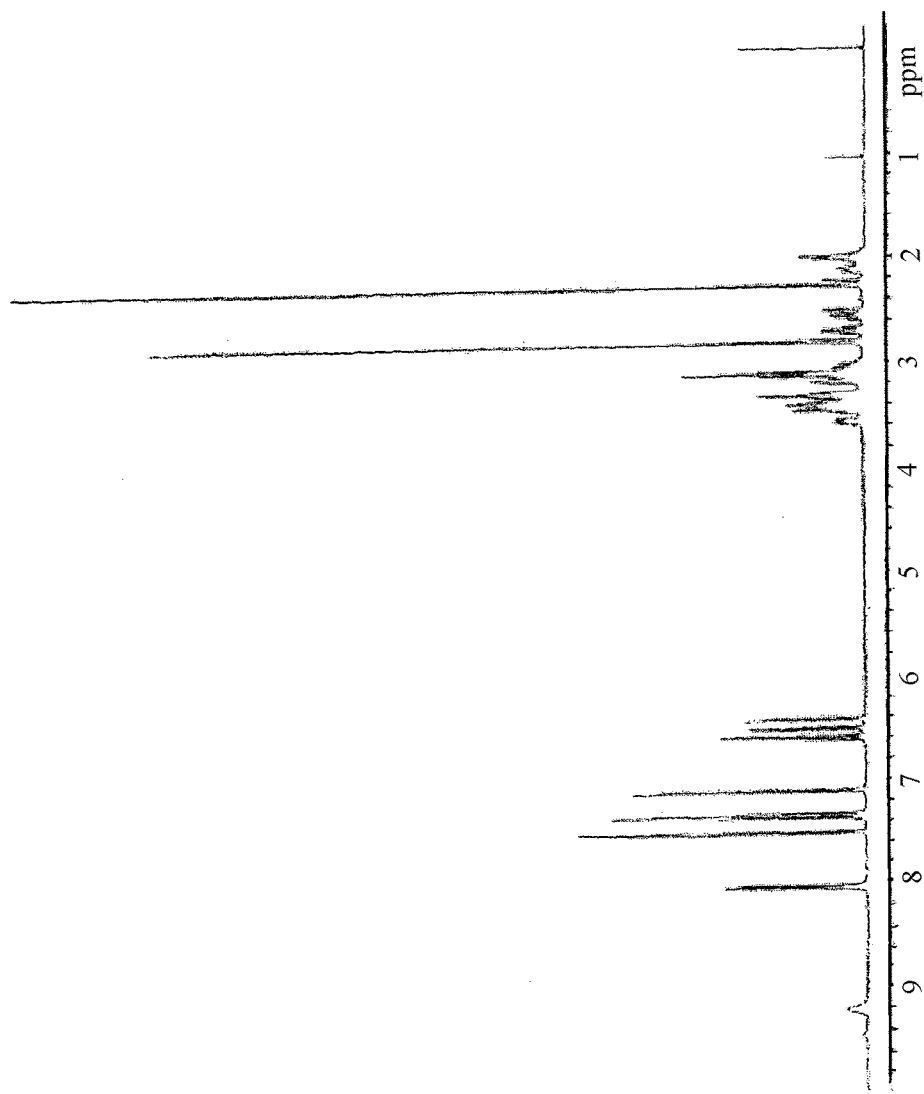
FIG. 4 (4/12) depicts a 400-MHz proton NMR spectrum of Salt Crystals Form A in DMSO-d6.
Figure 5:
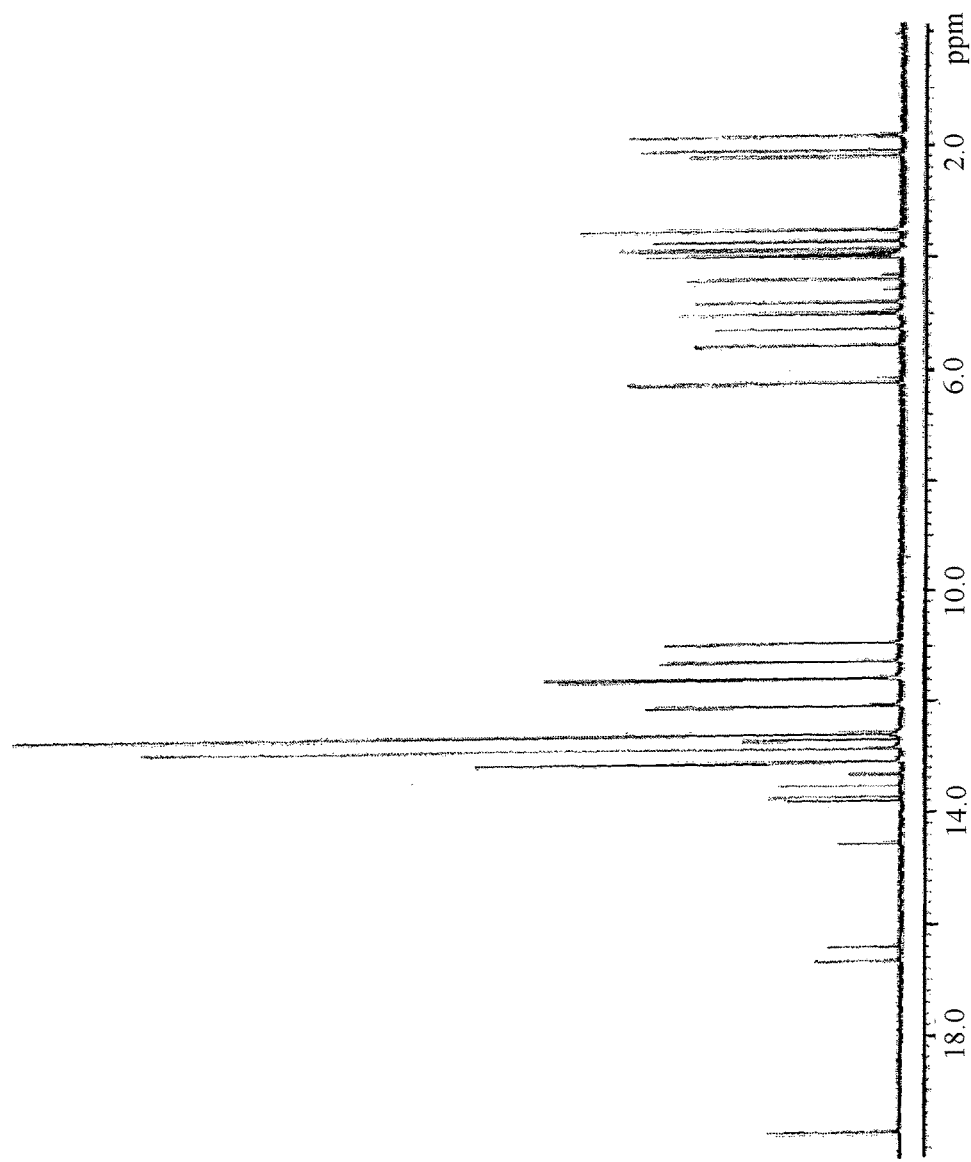
FIG. 5 (5/12) depicts a 100-MHz carbon NMR spectrum of Salt Crystals Form A in DMSO-d6.

The 400 MGz $^1$H (FIG. 4) and 100 MGz $^{13}$C (FIG. 5) NMR spectra for Salt Crystals Form A (Salt Crystals Form A, in DMSO-d6; TMS reference) are consistent with the structure of 4-((6bR,10aS)-3-methyl-2,3,6b,9,10,10a-hexahydro-1H-pyrido[3',4': 4,5]pyrrolo[1,2,3-de]quinoxalin-8 (7H)-yl)-1-(4-fluorophenyl)-1-butanone toluene sulfonic acid salt in all essential detail. Selected proton chemical shifts and coupling constants are listed in Table 2 and carbon chemical shifts are listed in Table 3.

The $^1$H NMR spectrum (FIG. 4) shows signals due to 36 protons consistent with the proposed structure. The $^{13}$C NMR spectrum (FIG. 5) shows 28 signals consistent with the 27 unique carbons in the proposed structure. $^1$H spectra assignments (in Table 2) and $^{13}$C spectral assignments for protonated carbons (in Table 3) are based on chemical shifts, COSY spectroscopy, HMQC spectroscopy and DEPT.

NMR spectra are recorded on a Varian 400 MHz Unity-plus NMR spectrometer equipped with a 5 mm $^1$H/$^{19}$F/$^{15}$N-$^{31}$P switchable probe. The $^1$H spectrum is recorded using 60° rf pulses and 16 transients. The $^{13}$C NMR spectrum is recorded using WALTZ proton decoupling, 60° rf pulses and 4096 transients.

TABLE 2

Proton NMR Chemical Shifts for Salt Crystals Form A

| δ1H* | Mult† | J§ | Int‡ | Tentative Assignment** |
|---|---|---|---|---|
| 9.22 | br s | | 1 | 25 |
| 8.04 | dd | 8.8 | 2 | 1 |
| 7.52 | d | 8 | 2 | 23 |
| 7.36 | t | 9.0 | 2 | 2 |
| 7.12 | dd | 8.4, 0.8 | 2 | 22 |
| 6.60 | t | 7.6 | 1 | 12 |
| 6.51 | d | 7.2 | 1 | 11 |
| 6.42 | d | 7.6 | 1 | 13 |
| 3.58 | dd | 12 | 1 | 9 |
| 3.50-3.39 | m | | 1, 1 | 16, 19 |
| 3.36-3.30 | m | | 1, 1, 1 | 15, 10, 16 |
| 3.20 | m | | 1 | 17 |
| 3.16-3.00 | m | 7.0 | 2, 2, 1 | 6, 8, 19 |
| 2.81 | s | | 3 | 14 |
| 2.70 | dt | 10.1, 2.9 | 1 | 15 |
| 2.55 | q | 11.2 | 1 | 9 |
| 2.50 | | | | DMSO-d6 |
| 2.27 | s | | 3 | 20 |
| 2.23 | br s | | 1 | 18 |
| 2.11 | m | | 1 | 18 |
| 2.01 | m | 7.6 | 2 | 7 |

*Chemical shift in ppm
**See structure for numbering
‡Signal integration in relative numbers of protons
†Multiplicity; s = singlet, d = doublet, t = triplet, m = multiplet, q = quartet, br = broad
§Proton-proton coupling in Hz

TABLE 3

Carbon NMR Chemical Shifts for Salt Crystals Form A

| δ13C* | MULT† | Tentative Assignment‡ |
|---|---|---|
| 197.2 | s | 5 |
| 166.3 & 163.8 | d | 3 |
| 145.3, 137.9, 137.3, | s, s, s, | 24, 21, 10a', |
| 135.2, 133.1 & 133.1, 126.8 | s, d, s | 4, 13a, 10a |
| 130.9 & 130.8 | d | 1 |
| 128.2 | s | 22 |
| 125.5 | s | 23 |
| 120.6 | s | 12 |
| 115.8 & 115.6 | d | 2 |
| 112.5 | s | 11 |
| 109.3 | s | 13 |
| 62.2 | s | 17 |
| 55.6 | s | 8 |
| 52.5 | s | 9 |
| 49.8 | s | 16 |
| 47.7 | s | 19 |
| 43.7 | s | 15 |
| 39.5 | | DMSO-d6 |
| 38.5 | s | 10 |
| 37.0 | s | 14 |
| 34.9 | s | 6 |
| 21.6 | s | 18 |
| 20.8 | s | 20 |
| 18.0 | s | 7 |

*Chemical shift in ppm
‡See structure for numbering
†Multiplicity; s = singlet, d = doublet Specific Rotation The specific rotation is recorded on a Perkin Elmer model 343 Plus polarimeter operating at the sodium D-Line (589.3 nm) and utilizing a 5-s sample integration time. The sample temperature is maintained at 25° C. with a temperature controlled water-jacketed cell. The sample is prepared by dissolving ca. 475 mg of Salt Crystals Form A with MeOH in a 50-mL volumetric flask.

Ultraviolet-Visible Spectrophotometry

Figure 6:
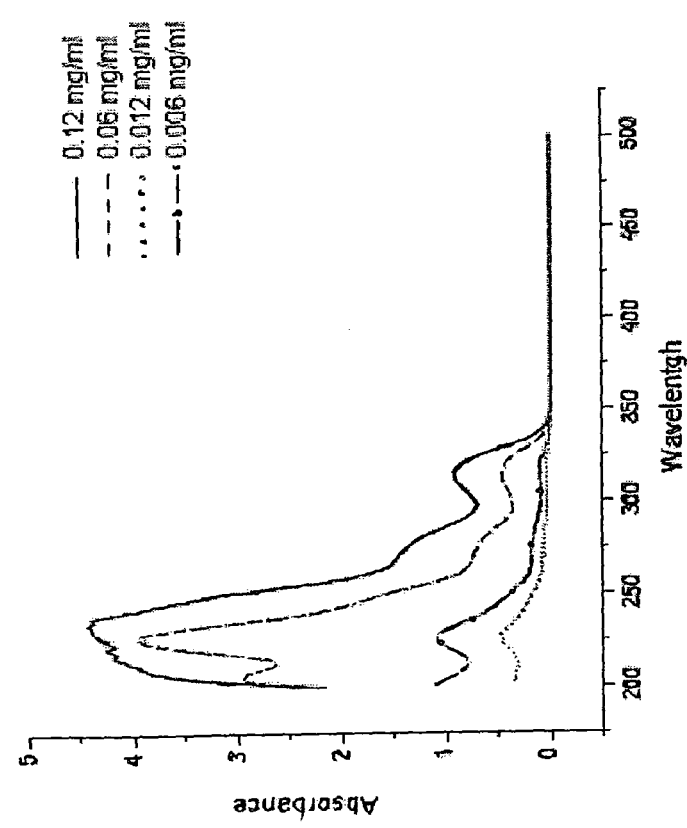
FIG. 6 (6/12) depicts a UV-Vis spectrum of Salt Crystals Form A in MeOH. The solid line depicts a spectrum of a sample having a concentration of 0.12 mg/mL. The ---- line depicts a spectrum of a sample having a concentration of 0.0.06 mg/mL. The ····· line depicts a spectrum of a sample having a concentration of 0.012 mg/mL. The —·— line depicts a spectrum of a sample having a concentration of 0.0006 mg/mL.

The ultraviolet/visible spectrum for Salt Crystals Form A can be found in FIG. 6. The spectra represent two different concentrations of Salt Crystals Form A in methanol. Two distinct maxima (227 nm □ 2 nm and 314 nm □ 2 nm) are found in the range of 200 nm to 500 nm. The molar extinction coefficient at 227 nm is calculated to be 43513 L*mol-1*cm-1. The molar extinction coefficient at 314 nm is calculated to be 4246 L*mol-1*cm-1. Calculation of Extinction Coefficient based on Salt Crystals Form A with a MW of 565.7. The spectra are recorded on a Cary 3 UV/Visible spectrophotometer using a 1.0 cm quartz cell. The samples are prepared in duplicate for each maxima wavelength at concentrations of ca. 0.12 mg/mL, 0.06 mg/mL for the maxima at 314 nm and ca. 0.012 mg/mL and 0.006 mg/mL for the maxima at 227 nm to optimize the spectra at each maxima examined. All samples are dissolved in methanol.

Residue on Ignition

Residue on ignition is performed according to USP 29/NF 24 (Supplement 2) 2006, General Chapter <281>. A sample of ca. 1 g is accurately weighed directly into a platinum crucible that has been previously ignited, cooled and weighed. The crucible is heated until the sample is thoroughly charred, then cooled. The residue is then moistened with approximately 1 mL of concentrated sulfuric acid, heated gently until white fumes no longer evolved, then ignited in a muffle furnace at 600±50° C. until all the carbon within the crucible was consumed. The sample is then cooled to room temperature in a desiccator. After cooling, the weight of residue is taken. The moistening with sulfuric acid, heating and igniting as before, using a 30 minute ignition period, is repeated, until two consecutive weighings of the residue does not differ by more than 0.5 mg. Results: Residue on Ignition=0.05%.

Elemental Analysis

The elemental analysis of sample Salt Crystals Form A is found to be consistent with the empirical formula. Samples are analyzed in duplicate and oxygen is determined by difference.

| | Element | | | | | |
|---|---|---|---|---|---|---|
| | Carbon | Hydrogen | Nitrogen | Oxygen[3] | Fluorine | Sulfur |
| Percent Experimental Value[1] | 65.48 | 6.63 | 7.44 | 11.15 | 3.39 | 5.92 |
| Percent Theoretical Value[2] | 65.82 | 6.41 | 7.43 | 11.31 | 3.36 | 5.67 |
| Percent Difference | −0.34 | 0.22 | 0.01 | −0.16 | 0.03 | 0.25 |

[1]Average (n = 2)
[2]ChemWindow V.5.1
[3]Oxygen determined by difference (Halogens interfere with the direct measurement of Oxygen)

X-Ray Powder Diffraction (XRPD)

Figure 7:
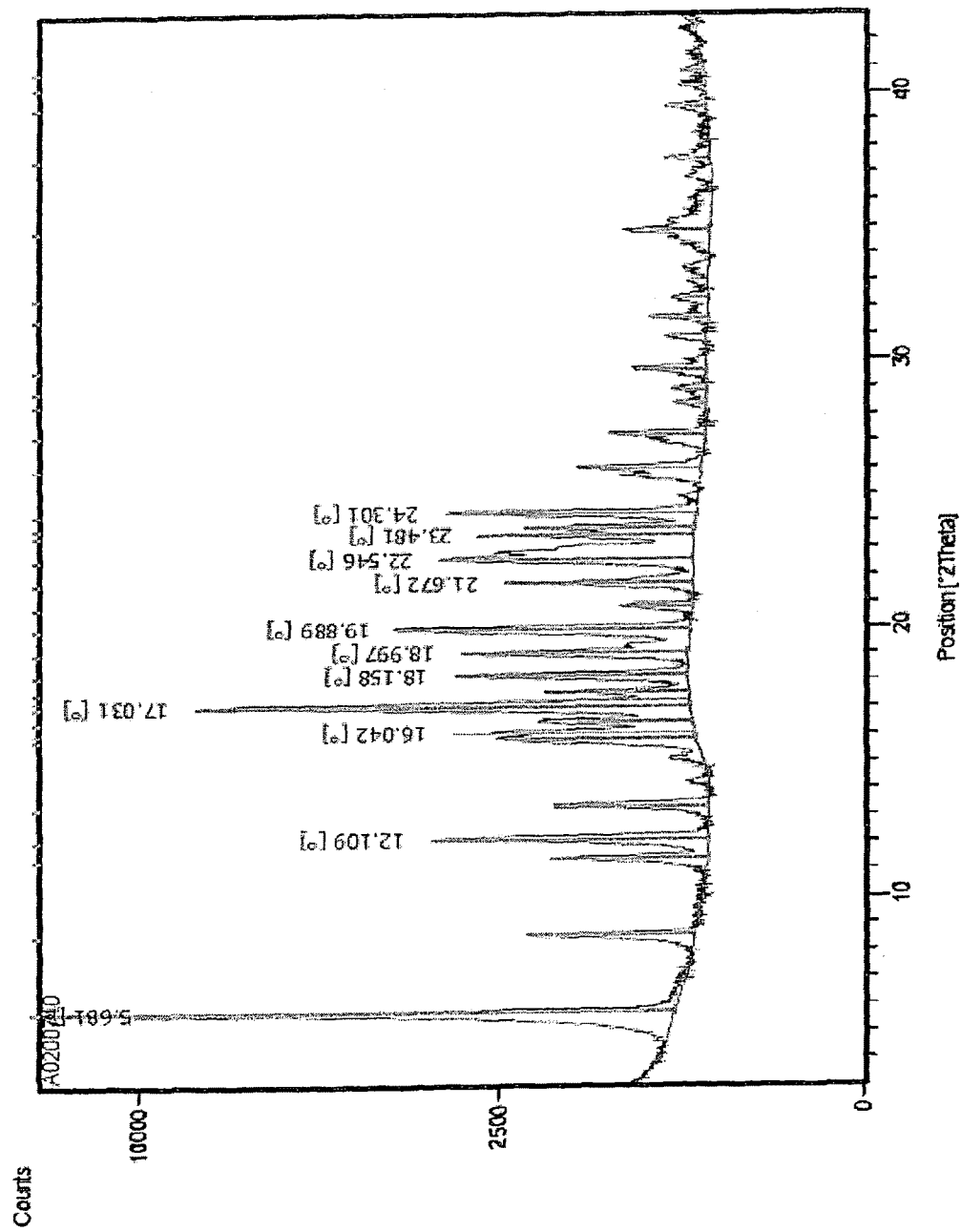
FIG. 7 (7/12) depicts X-Ray Powder Diffraction Pattern of Salt Crystals Form A (Cu Kα Radiation).
Figure 7A:
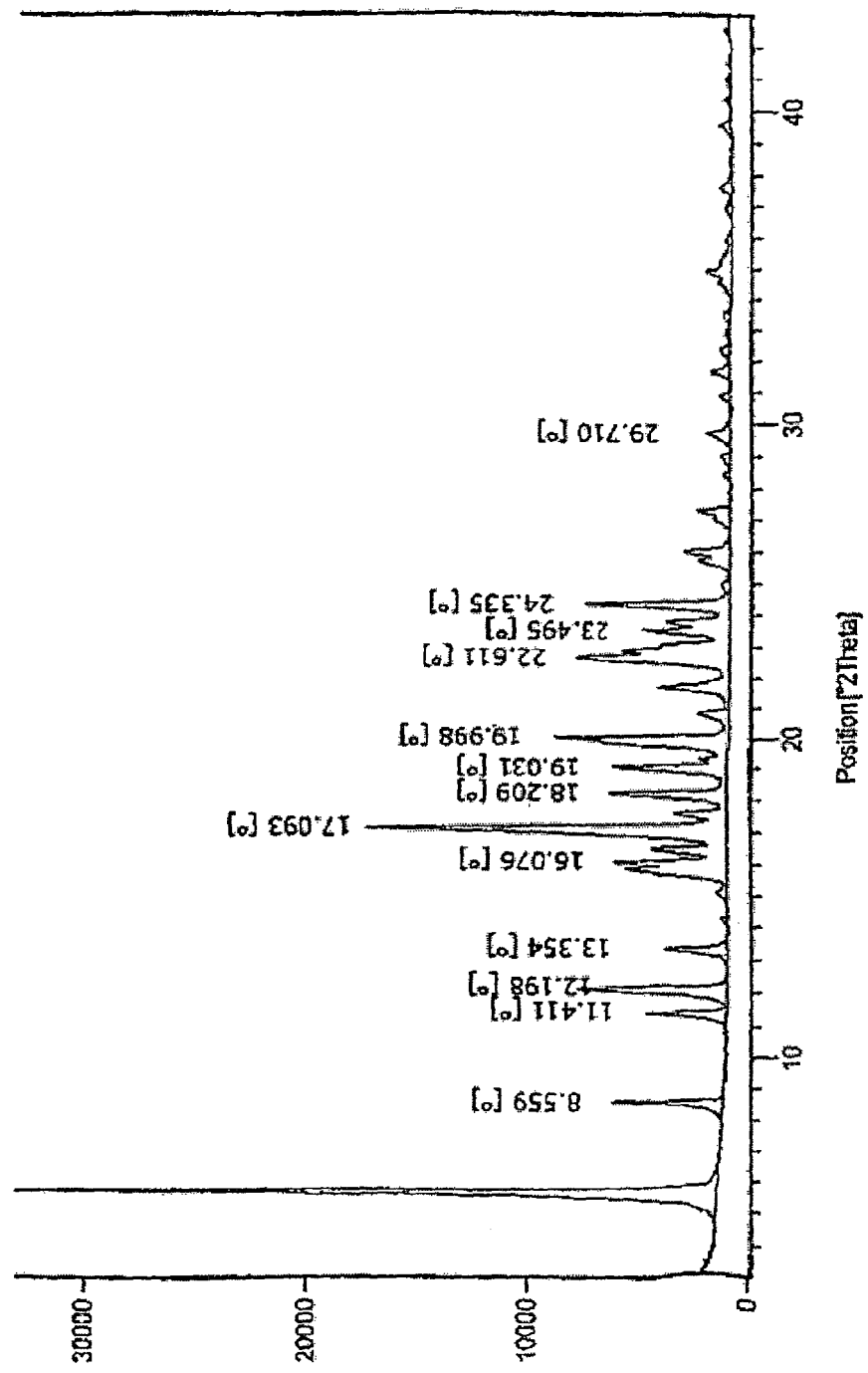
FIG. 7A (8/12) depicts X-Ray Powder Diffraction Pattern of Salt Crystals Form A.

The XRPD pattern of Salt Crystals Form A is shown in FIG. 7 along with some of the more prominent 2θ values. Table 4 shows a listing of the more prominent 2θ angles, d-spacings and relative intensities.

XRPD data is collected at ambient temperature on a PANalytical X'Pert θ/θ diffractometer, operating with copper radiation at 45 kV and 40 mA, using an X'Celerator detector. Unmilled sample is placed on a flat stainless steel sample holder and leveled using a glass microscope slide. Incident beam optics consists of ⅛° fixed divergence slit, ¼° fixed anti-scatter slit, 0.04 rad Soller slit and nickel filter to filter out Kα2 radiation. Data is collected at 3° to 43° 2θ. A standard PC with Windows XP® operating system and PANalytical X'Pert Data Collector v 2.1a are used. X'Pert Data Viewer v 1.1a is used to plot the data. The unit is calibrated annually using NBS silicon powder as a standard.

TABLE 4

Salt Crystals Form A Some of the More Prominent 2θ Angles, D-Spacing and Relative Intensities (Cu Kα Radation)

| POSITION (°2θ) | HEIGHT (Cts) | FWHM (°2θ) | D-SPACING (Å) | RELATIVE INTENSITY (%) |
|---|---|---|---|---|
| 5.6811 | 11807.77 | 0.1658 | 15.54391 | 100.00 |
| 8.6140 | 1582.45 | 0.1671 | 10.37709 | 13.40 |
| 11.3750 | 1379.81 | 0.1863 | 7.77273 | 11.89 |
| 12.1088 | 3074.71 | 0.2072 | 7.30333 | 26.04 |
| 13.3354 | 1329.25 | 0.1838 | 6.63416 | 11.26 |
| 15.7948 | 1845.19 | 0.2650 | 5.60626 | 15.63 |
| 16.0419 | 2633.59 | 0.1568 | 5.52046 | 22.30 |
| 16.4461 | 976.96 | 0.5368 | 5.38570 | 8.27 |
| 17.0309 | 7890.92 | 0.2151 | 5.20205 | 66.83 |
| 17.2606 | 1283.83 | 4.0000 | 5.13334 | 10.87 |
| 17.5531 | 1328.92 | 0.1966 | 5.04844 | 11.25 |
| 18.1581 | 2550.85 | 0.1871 | 4.88158 | 21.60 |
| 18.9968 | 2449.84 | 0.2219 | 4.66792 | 20.75 |
| 19.8889 | 3546.82 | 0.2456 | 4.46051 | 30.04 |
| 20.7510 | 559.67 | 0.0792 | 4.27711 | 4.74 |
| 21.6724 | 1855.28 | 0.1758 | 4.09730 | 15.71 |
| 22.5463 | 2825.63 | 0.2478 | 3.94041 | 23.93 |
| 23.4815 | 2226.62 | 0.1730 | 3.78556 | 18.86 |
| 23.7411 | 1604.25 | 0.1854 | 3.74475 | 13.59 |
| 24.3006 | 2777.58 | 0.1798 | 3.65978 | 23.52 |
| 25.9394 | 874.95 | 0.3670 | 3.43216 | 7.41 |
| 27.2321 | 673.90 | 0.2791 | 3.27209 | 5.71 |
| 28.3782 | 192.47 | 0.1700 | 3.14250 | 1.63 |
| 28.9055 | 158.09 | 0.1331 | 3.08636 | 1.34 |
| 29.6695 | 493.21 | 0.2567 | 3.00860 | 4.18 |
| 31.6106 | 374.66 | 0.1619 | 2.82814 | 3.17 |
| 32.2950 | 211.18 | 0.2236 | 2.76975 | 1.79 |
| 34.8530 | 401.29 | 0.6501 | 2.57211 | 3.40 |
| 37.5435 | 283.20 | 0.1845 | 2.39373 | 2.40 |
| 39.4972 | 264.36 | 0.2221 | 2.27971 | 2.24 |
| 40.2502 | 140.53 | 0.1475 | 2.23878 | 1.19 |
| 40.8303 | 125.14 | 0.1353 | 2.20830 | 1.06 |

Figure 7B:
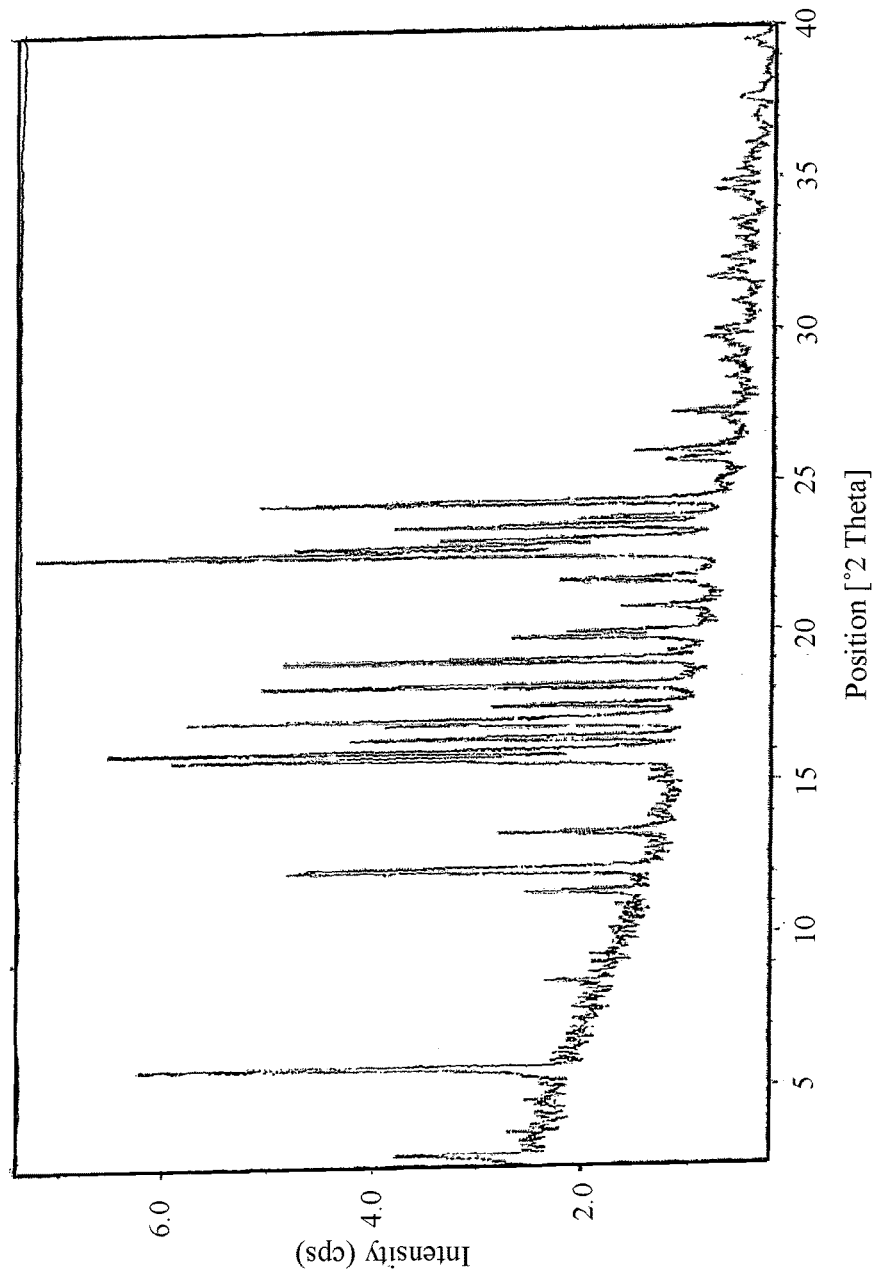
FIG. 7B (9/12) depicts an X-Ray Powder Diffraction Pattern of Salt Crystals Form A. Panalytical X-Pert Pro MPD PW3040 Pro. X-ray Tube: Cu(I.54059 Å. Voltage: 15 kV. Amperage: 10 mA. Scan Range: 1.01-39.98*2θ. Step Size: 0.017*2θ. Collection Time: 721 s. Scan Speed: 3.2*/min. Slit: DS: ½°. SS: ¼°. Revolution Time 1.0 s. Mode: Transmission.

XRPD patterns of FIG. 7B are collected using a PANalytical X'Pert Pro diffractometer. An incident beam of Cu Kα radiation is produced using an Optix long, fine-focus source. An elliptically graded multilayer mirror is used to focus the Cu Kα X-rays of the source through the specimen and onto the detector. Data are collected and analysed using X'Pert Pro Data Collector software (v.2.2b). Prior to the analysis, a silicon specimen (NIST SRM 640c) is analyzed to verify the Si 111 peak position. The specimen is sandwiched between 3 μm thick films, analyzed in transmission geometry, and rotated to optimize orientation statistics. A beam-stop is used to minimize the background generated by air scatting. Anti-scattering extension and He are not used. Soller slits are used for the incident and diffracted beam to minimize axial divergence. Diffraction patterns are collected using a scanning position-sensitive detector (X'Celerator) located 240 mm from the specimen. The data acquisition parameters for each pattern are displayed above the image in the Data section.

Differential Scanning Calorimetry (DSC)

Figure 8:
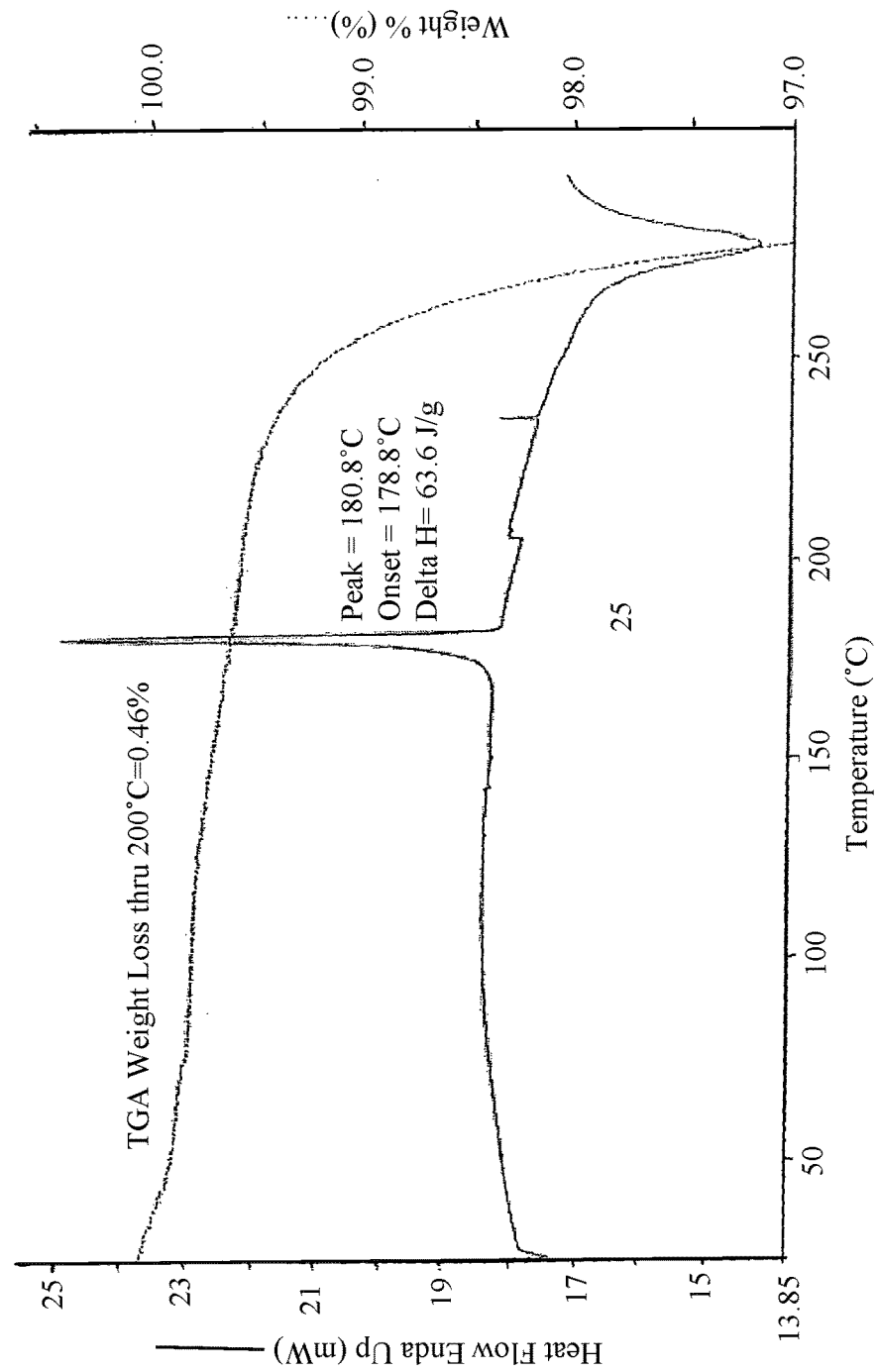
FIG. 8 (10/12) depicts a DSC and TGA Scans for Salt Crystals Form A Taken at a 10° C./min Scan Rate.

The DSC scan for Salt Crystals Form A is shown in FIG. 8. The DSC scan shows a single endotherm with an onset temperature of 178.8° C., peak temperature of 180.8° C., and ΔH=63.6 J/g. DSC measurements are made using a Perkin Elmer Pyris 1 DSC system equipped with an intracooler 2P refrigeration unit. The Pyris 1 DSC is purged with nitrogen. Calibration is performed prior to analysis using an Indium standard at a 10° C./min heating rate. Approximately 1.7 mg of sample is weighed on a Sartorius microbalance in a tared Perkin Elmer 30 μL universal aluminum pan with holes in the lid, and sealed using a Perkin Elmer pan crimper press. The sample is heated from room temperature to 300° C. at 10° C./min.

Thermo Gravimetric Analysis (TGA)

The TGA scan for Salt Crystals Form A is shown in FIG. 8. The TGA analysis shows two regions of weight loss with a total weight loss of 0.46% through 200° C. TGA measurements are collected using a Perkin Elmer Pyris 1 TGA system purged with nitrogen. A 100-mg standard weight and Ni metal are used to verify balance and temperature calibrations, respectively. A sample of Salt Crystals Form A is heated from room temperature to 300° C. at 10° C./min.

Melting Point

A melting point determination is performed on an electro thermal capillary melting point apparatus. The sample is heated from a temperature of 160° C. at a ramp rate of 2° C./min. Capillary melting point data exhibit no true melting point as the material decomposes over the region of 176.8 through 181.0° C. Thus the endotherm does not represent melting.

EXAMPLE 2

Preparation of the Salt Crystals Form B

Equip a 500 mL 3-neck round bottom flask with a mechanical stirrer, nitrogen inlet, drying tube and thermocouple. Dissolve the starting material 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone in toluenesulfonic acid addition salt (7.62 g, 0.01936 mol, 1 equivalent) in Ethanol (200 proof (50 mL). Charge the solution of starting material in ethanol (step 2) to the flask. Add p-toluenesulfonic acid monohydrate (3.68 g, 0.01936 mol, 1 eq) in one portion followed by charcoal (3 g). Heat the resulting mixture to 75-80° C. and stir at this temperature for 5-10 minutes. After this time remove the charcoal by filtration and wash the filter cake with Ethanol (3×30 mL). Transfer the combined filtrate to a 1 L 3-neck round bottom flask equipped with a mechanical stirrer, nitrogen inlet, drying the tube and thermocouple and placed in a cooling tub. Cool the solution to 0-5° C. Suspension forms during cooling. Dilute this suspension with heptane and stir at 0-5° C. for a minimum of 13 hours at this temperature. Collect the solids by filtration. Wash the solids with cold Ethanol (20 mL, 0-5° C.) and then with heptane (room temperature, 50 mL). Dry the solids in a vacuum oven at 35° C. to constant weight. Yield 7.2 g, 0.0127 mol, 65.7%. HPLC: 96.4%. Chiral HPLC: de 100%. Melting point 182-183° C.

EXAMPLE 3

Preparation of the Salt Crystals Form B

Dissolve the starting material, 66-H-113 Peak 1 (9.32 g, 0.02368 mol, 1 eq) in Ethanol (200 proof, 80 mL). Add charcoal (0.5 g) and stir the resulting mixture for 10-20 minutes at room temperature. After this time remove charcoal by filtration. Wash the filter cake with Ethanol (2×30 mL). Charge the solution of starting material in ethanol (from the previous step) to a 1 L 3-neck round bottom flask with a mechanical stiner, nitrogen inlet, drying tube and thermocouple the flask and placed in a cooling tub. Add p-Toluenesulfonic acid monohydrate (4.51 g, 0.02368 mol, 1 eq) in one portion at room temperature. Clear amber solution forms. Soon solids stat to form. Cool the resulting suspension to 0-5° C., stir for 1 hour at this temperature and then dilute with heptane (300 mL). Stir the suspension for a minimum of 13 hours at 0-5° C. After this time, obtain the solids by filtration (tan). Wash the solids cold with heptane (room temperature, 50 mL). Dry the solids in a vacuum oven at 35° C. to constant weight. Yield: 10.93 g, 0.01932 mol, 81.59%.

Figure 9:
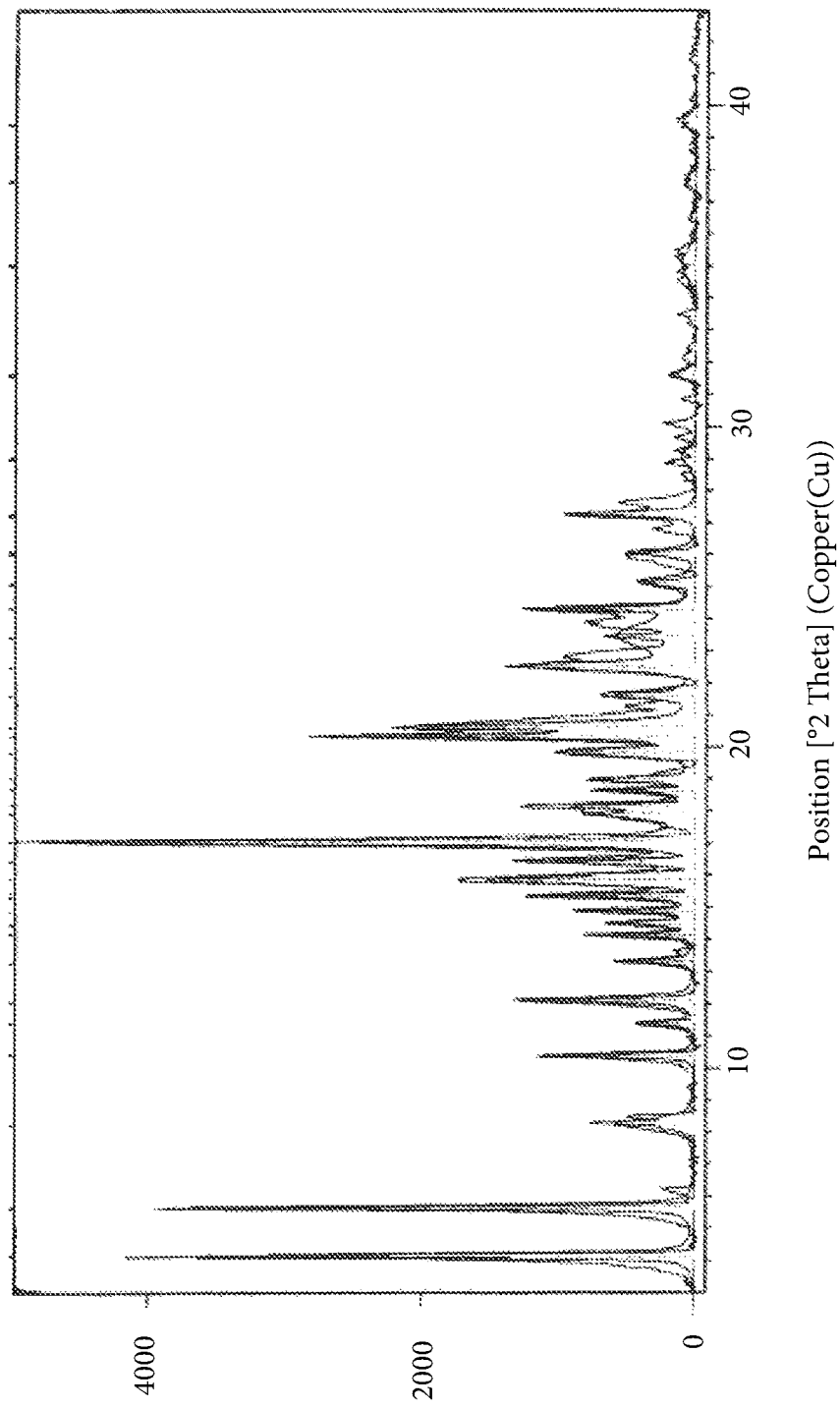
FIG. 9 (11/12) depicts an X-Ray Powder Diffraction Pattern of Salt Crystals Form B.
Figure 10:
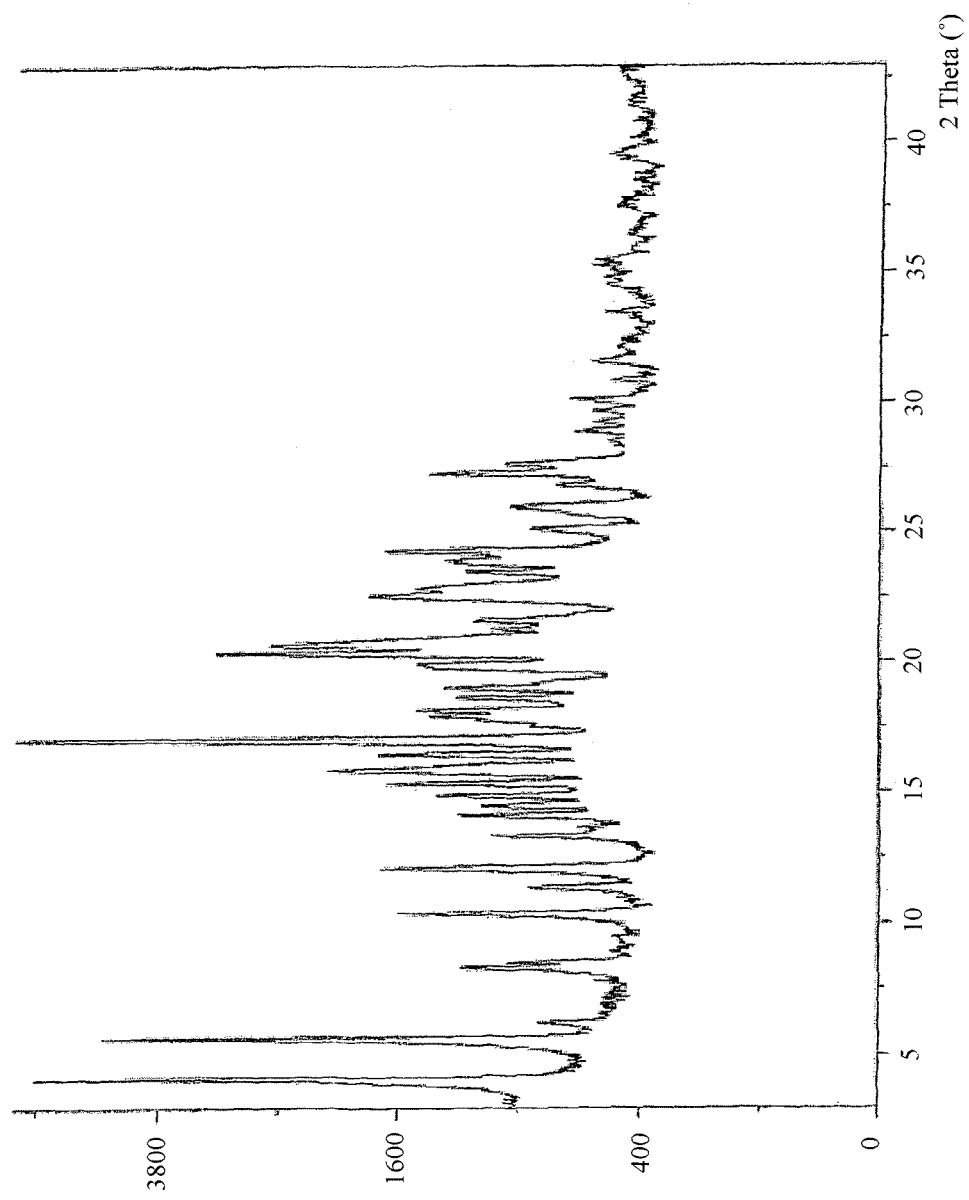
FIG. 10 (12/12) depicts an X-Ray Powder Diffraction Pattern of Salt Crystals Form B.

Salt Crystals of Form B has the following XRPD: The XRPD pattern of Salt Crystals Form B is shown in FIG. 9. Table 5 shows a listing of the more prominent 2θ angles, d-spacings and relative intensities.

TABLE 5

| Pos. [°2Th.] | Height [cts] | FWHM [°2Th.] | d-spacing [Å] | Rel. Int. [%] |
| --- | --- | --- | --- | --- |
| 4.1373 | 3800.46 | 0.1299 | 21.35763 | 83.44 |
| 5.6541 | 3600.03 | 0.1299 | 15.63088 | 79.04 |
| 8.2430 | 526.80 | 0.3897 | 10.72658 | 11.57 |
| 10.3839 | 1089.03 | 0.1299 | 8.51937 | 23.91 |
| 11.3760 | 389.27 | 0.1624 | 7.77853 | 8.55 |
| 12.1103 | 1193.49 | 0.1948 | 7.30844 | 26.20 |
| 13.3099 | 544.61 | 0.1624 | 6.65232 | 11.96 |
| 14.1235 | 732.42 | 0.1299 | 6.27088 | 16.08 |
| 14.4743 | 583.24 | 0.1624 | 6.11969 | 12.81 |
| 14.8763 | 797.18 | 0.1299 | 5.95520 | 17.50 |
| 15.3532 | 1091.73 | 0.1624 | 5.77130 | 23.97 |
| 15.8535 | 1531.27 | 0.2922 | 5.59028 | 33.62 |

TABLE 5-continued

| Pos. [°2Th.] | Height [cts] | FWHM [°2Th.] | d-spacing [Å] | Rel. Int. [%] |
| --- | --- | --- | --- | --- |
| 16.4465 | 1139.43 | 0.1948 | 5.39000 | 25.02 |
| 17.0544 | 4554.66 | 0.1948 | 5.19923 | 100.00 |
| 17.9466 | 668.96 | 0.3897 | 4.94274 | 14.69 |
| 18.1622 | 884.32 | 0.1299 | 4.88454 | 19.42 |
| 18.6277 | 693.40 | 0.1299 | 4.76350 | 15.22 |
| 18.9621 | 714.43 | 0.1624 | 4.68024 | 15.69 |
| 19.8255 | 884.11 | 0.2598 | 4.47833 | 19.41 |
| 20.3507 | 2433.40 | 0.1624 | 4.36392 | 53.43 |
| 20.6196 | 1910.18 | 0.2598 | 4.30762 | 41.94 |
| 21.6034 | 604.41 | 0.2598 | 4.11363 | 13.27 |
| 22.4973 | 1188.22 | 0.2598 | 3.95215 | 26.09 |
| 23.4609 | 494.32 | 1.0391 | 3.79196 | 10.85 |
| 24.3083 | 1191.59 | 0.1299 | 3.66167 | 26.16 |
| 25.1377 | 399.77 | 0.2598 | 3.54270 | 8.78 |
| 26.0351 | 473.87 | 0.2273 | 3.42260 | 10.40 |
| 27.2489 | 970.43 | 0.1624 | 3.27282 | 21.31 |
| 29.0199 | 91.17 | 0.6494 | 3.07701 | 2.00 |
| 31.5733 | 191.51 | 0.2598 | 2.83374 | 4.20 |
| 35.0279 | 94.76 | 1.0391 | 2.56178 | 2.08 |
| 37.6449 | 72.13 | 0.5196 | 2.38949 | 1.58 |
| 39.4614 | 89.16 | 0.5845 | 2.28359 | 1.96 |

EXAMPLE 4

Preparation of the Solid Salt or Salt Crystals of the Present Invention

Dissolve the starting material, 66-H-113 Peak 1 (5.28 g, 0.01342 mol, 1 eq) in Ethanol (200 proof, 35 mL). After this time, remove the charcoal by filtration. Wash the filter cake with 1 Ethanol (2×15 mL). Charge the solution of starting material in ethanol (from the previous step) to a 500 in L 3-neck round bottom flask equipped with a mechanical stirrer, nitrogen inlet, drying tube and thermocouple. The flask is placed in a cooling tub. Add p-Toluenesulfonic acid monohydrate (4.51 g, 0.02368 mol, 1 eq) in one portion at room temperature. Clear dark amber solution forms. Soon solids start to form. Cool the resulting suspension to 0-5° C. stir for 1 hour at this temperature and then dilute with heptane (200 mL). Stir the suspension for a minimum of 13 hours at 0-5'C. After this time remove the solids by filtration (tan). Wash the solids cold with heptane (room temperature, 40 mL). Dry the solids in a vacuum oven at 35° C. to constant weight. Yield: 5.95 g, 0.010617 mol, 78.37%

EXAMPLE 5

Preparation of the Solid Salt or Salt Crystals of the Present Invention

Crude free base is dissolved in EtOH (3000 mL), and is transferred to a 12 L, 3-necked, round-bottomed flask equipped with a mechanical stirrer, a $N_2$ inlet, and a temperature probe. To the stirred solution is then added 178.3 g of pTSA monohydrate (0.94 mol, 1 equiv relative to the crude free base). The batch is stirred at rt for ca. 1 h, and then the internal temperature is reduced to 2 to 4° C. with an ice bath. The batch is stirred at 2 to 4° C. for another 1 h, and the batch becomes a brownish white slurry. To the batch is then added heptane (6000 mL) through an addition funnel slowly in ca. 3 h. The resultant mixture is stirred at 2 to 4° C. for another 1 h, and is stored in a dark cold room for ca. 15 h. The batch is then filtered, and the solid is rinsed with heptane (1000 mL). After drying in a vacuum oven at 35 to 40° C. for 4 h, 345.8 g (61% yield) of a tan to brown solid was obtained. HPLC analysis showed the desired product at 96.9% purity. LC-MS analysis showed a major peak with M/e=394 (M+1). Chiral HPLC analysis showed the desired enantiomer (first eluting peak) with ca. 99.7% e.e. $^1$H NMR (CDCl$_3$, 300 MHz) δ 2.12-2.32 (m, 4H), 2.35 (s, 3H), 2.52-2.70 (m, 2H), 2.80-2.94 (m, 1H), 2.90 (s, 3H), 3.02-3.24 (m, 5H), 3.26-3.42 (m, 4H), 3.50-3.76 (m, 4H), 6.48 (d, J=7.8 Hz, 1H), 6.55 (d, J=7.2 Hz, 1H), 6.74 (t, J=7.5 Hz, 1H), 7.04-7.14 (m, 2H), 7.18 (d, J=8.1 Hz, 2H), 7.78 (dd, J=6.3 Hz, J'=1.5 Hz, 2H),7.92-7.98 (m, 2H), 10.60 (bs, 1H).

The invention claimed is:

1. A 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone toluenesulfonic acid addition salt crystal form, wherein said salt crystal form exhibits an X-ray powder diffraction pattern comprising at least two peaks selected from the group consisting of 5.68°, 12.11°, 16.04°, 17.03°, 18.16°, 19.00°, 21.67°, 22.55°, 23.48° and 24.30°±0.2° 2θ.

2. A pharmaceutical composition comprising the salt crystal form according to claim 1, as active ingredient, together with a pharmaceutically acceptable diluent or carrier.

* * * * *